United States Patent [19]

Yamaguchi et al.

[11] Patent Number: 4,754,068

[45] Date of Patent: Jun. 28, 1988

[54] 1,3-BIS(3-AMINOPHENOXY)-5-HALOGENOBENZENES AND PROCESS FOR THEIR PREPARATION

[75] Inventors: Keizaburo Yamaguchi; Yukihiro Yoshikawa; Yoshimitsu Tanabe; Kenichi Sugimoto; Akihiro Yamaguchi, all of Tokyo, Japan

[73] Assignee: Mitsui Toatsu Chemicals, Inc., Tokyo, Japan

[21] Appl. No.: 940,201

[22] Filed: Dec. 15, 1986

Related U.S. Application Data

[63] Continuation of Ser. No. 636,168, Jul. 31, 1984, abandoned.

[30] Foreign Application Priority Data

Oct. 21, 1983 [JP] Japan ................................ 58-196226

[51] Int. Cl.$^4$ ............................................. C07C 93/14
[52] U.S. Cl. .................................... 564/430; 528/127; 528/128
[58] Field of Search ........................................ 564/430

[56] References Cited

U.S. PATENT DOCUMENTS

3,879,349  4/1975  Bilow et al. .......................... 528/127
4,222,962  9/1980  Pellegrini, Jr. ....................... 564/430
4,469,893  9/1984  Tang et al. ........................ 564/430 X
4,539,428  9/1985  Merrell et al. ....................... 564/430

OTHER PUBLICATIONS

Kirk–Othmer, *Encyclopedia of Chemical Technology*, Third Ed., vol. 9, John Wiley & Sons, Inc.: New York, 1980, pp. 384–385.
Morrison et al., *Organic Chemistry*, Third Ed., Allyn and Bacon, Inc.: Boston, 1973, pp. 359–361, 556–558.
March, *Advanced Organic Chemistry, Reactions, Mechanisms, and Structure*, 3rd Ed., pp. 584–587 and 589 (1985).
Pine et al., *Organic Chemistry*, pp. 649–652 (1980).

*Primary Examiner*—Floyd D. Higel
*Assistant Examiner*—Carolyn S. Greason
*Attorney, Agent, or Firm*—Jeffers, Hoffman & Niewyk

[57] ABSTRACT

1,3-Bis(3-aminophenoxy)-5-halogenobenzenes represented by the formula (I):

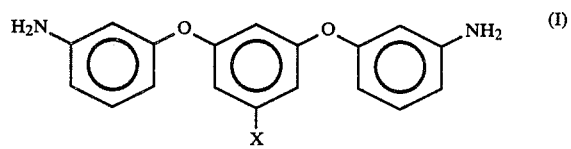

wherein X is a chlorine or bromine atom, are novel compounds and can be prepared by reacting trihalogenobenzenes represented by the formula (II):

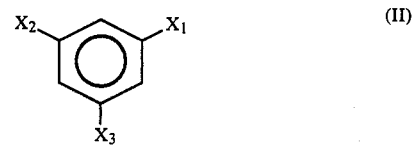

wherein $X_1$, $X_2$ and $X_3$ are each a chlorine or bromine atom, with 3-aminophenol in the presence of a dehydrohalogenating agent.

16 Claims, No Drawings

1,3-BIS(3-AMINOPHENOXY)-5-HALOGENOBENZENES AND PROCESS FOR THEIR PREPARATION

This is a continuation of prior application Ser. No. 636,168, filed on July 31, 1984, now abandoned.

BACKGROUND OF THE INVENTION

The present invention relates to 1,3-bis(3-aminophenoxy)-5-halogenobenzenes and a process for their preparation. 1,3-Bis(3-aminophenoxy)-5-halogenobenzenes are novel compounds which have not been disclosed in literature and a process for their preparation is not known at all.

This inventor has investigated monomers suitable for preparing heat-resistant resins, and now has found that novel 1,3-bis(3-aminophenoxy)-5-halogenobenzenes can be obtained in high yields by the condensation of 1,3,5-trihalogenobenzenes, which have been widely used as starting materials of pesticides, pharmaceuticals or solvents, and 3-aminophenol. The present invention has been accomplished on the basis of this finding.

SUMMARY OF THE INVENTION

It is an object of the present invention to provide important intermediates for preparing 1,3-bis(3-aminophenoxy)benzene, which is known as a monomer for preparing heat-resistant polymers, such as polyamide, polyimide or acetylene-terminated polyimide which is one of polymers having the most improved heat resistance and is prepared from 1,3-bis(3-aminophenoxy)benzene, 3,3′,4,4′-benzophenonetetracarboxylic dianhydride and 3-aminophenylacetylene (U.S. Pat. Nos. 3,845,018 and 3,879,349).

It is another object of the present invention to provide a process for the preparation of 1,3-bis(3-aminophenoxy)-5-halogenobenzenes which are intermediates suitable for preparing 1,3-bis(3-aminophenoxy)benzene and are represented by the general formula (I):

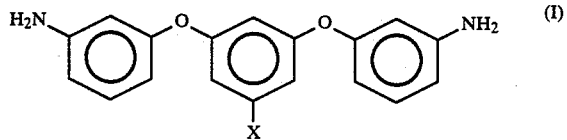

wherein X is a chlorine or bromine atom, which comprises reacting 1,3,5-trihalogenobenzene represented by the general formula (II):

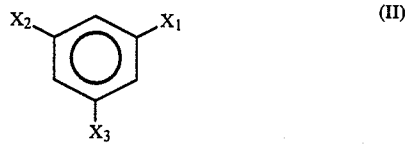

wherein $X_1$, $X_2$ and $X_3$ are each a chlorine or bromine atom,
with 3-aminophenol in the presence of a dehydrohalogenating agent.

DETAILED DESCRIPTION OF THE INVENTION

According to the present invention, 1,3-bis(3-aminophenoxy)-5-halogenobenzenes are prepared by the reaction of one molecule of 1,3,5-trihalogenobenzene and two molecules of 3-aminophenol in the presence of a dehydrohalogenating agent in an organic solvent. Unlike ordinary Ullman reaction, no copper compounds are necessary as an accelerator in the process according to the present invention. Furthermore, the process according to the present invention has an advantage in that the condensation reaction can proceed easily under a mild condition by simply removing water to produce 1,3-bis(3-aminophenoxy)-5-halogenobenzene in a high yield.

Examples of the 1,3,5-trihalogenobenzenes represented by the general formula (II) include 1,3,5-trichlorobenzene, 1,3-dichloro-5-bromobenzene, 1,3-dibromo-5-chlorobenzene and 1,3,5-tribromobenzene.

When 1,3,5-trichlorobenzene or 1,3-dichloro-5-bromobenzene is used, 1,3-bis(3-aminophenoxy)-5-chlorobenzene will be obtained as a product. When 1,3-dibromo-5-chlorobenzene is used, 1,3-bis(3-aminophenoxy)-5-chlorobenzene will be obtained as a main product. When 1,3,5-tribromobenzene is used, 1,3-bis(3-aminophenoxy)-5-bromobenzene will be obtained.

The amount of 3-aminophenol used is from 2 to 5 mol, preferably from 2.1 to 3 mol per mol of 1,3,5-trihalogenobenzene used.

Examples of the dehydrohalogenating agents to be used include hydroxides, carbonates, bicarbonates and alkoxides of alkali metals. More particularly, they include potassium hydroxide, sodium hydroxide, lithium hydroxide, potassium carbonate, sodium carbonate, lithium carbonate, potassium bicarbonate, sodium bicarbonate, potassium ethoxide, potassium, isopropoxide, sodium methoxide, sodium ethoxide, lithium ethoxide or the like. One or more of these dehydrohalogenating agents may be used.

The amount of the dehydrohalogenating agent used is at least an equivalent amount, preferably from 1 to 1.5 times the equivalent amount of 3-aminophenol usedd.

In a process according to the present invention, solvents may be used. Preferably aprotic polar solvents are used. Examples of such aprotic polar solvents include N-methylformamide, N,N-dimethylformamide, N,N-dimethylacetamide, dimethyl sulfoxide, dimethyl sulfone, sulfolane, N-methylpyrrolidone, 1,3-dimethyl-2-imidazolidinone and hexamethylphosphoric triamide. Though the amount of solvents used is not limited, it is generally from 1 to 10 times the weight of starting materials used.

In general, the reaction temperature is in the range of 120° to 240° C., the range of 140° to 220° C. being preferred.

The process of the present invention can be carried out according to the following general procedure: a specified amount of 3-aminophenol, a dehydrohalogenating agent and a solvent are charged in a reaction vessel, the 3-aminophenol is converted into its alkali metal salt and then 1,3,5-trihalogenobenzene is added to the vessel to accomplish the condensation. Alternatively, the process of the present invention can be carried out according to another procedure: that is, 3-aminophenol, a dehydrohalogenating agent, a solvent and 1,3,5-trihalogenobenzene are charged simultaneously and the mixture is heated to accomplish the condensation.

When water generates in the reaction system, it can be gradually removed by passing gaseous nitrogen through the system. However, in general, it is removed from the reaction system by azeotropic distillation by the use of a small amount of benzene, toluene, xylene, chlorobenzene or the like. After the completion of the reaction, the reaction mixture is optionally concentrated, and the concentrated or unconcentrated reaction mixture is poured into water to give a crude product. The crude product can be purified by converting it into its mineral acid addition salt such as hydrochloride.

The end of the reaction can be determined by monitoring the reduction in the amount of an unreacted intermediate (e.g. a monoaminophenoxy compound) by thin-layer chromatography or high-performance liquid chromatography.

According to the procedure as described above, 1,3-bis(3-aminophenoxy)-5-chlorobenzene and 1,3-bis(3-aminophenoxy)-5-bromobenzene, which correspond to the compounds of the general formula (II) wherein X is a chlorine atom or a bromine atom, can be obtained.

The following examples are to further illustrate the compounds according to the present invention and the processes for their preparation.

EXAMPLE 1

120 g (1.1 mol) of 3-aminophenol, 75 g (1.15 mol) of granular potassium hydroxide having a purity of 86%, 500 ml of 1,3-dimethyl-2-imidazolidinone (hereinafter referred to as "DMI") and 50 ml of xylene are charged in a 2 l flask equipped with a stirrer and a water separator. The temperature of the content was raised under stirring while passing gaseous nitrogen through it, so that the xylene in the reaction system was refluxed to remove water fromed in the system by a water separator. The amount of water distilled away was 20.5 ml.

A solution of 91 g (0.5 mol) of 1,3,5-trichlorobenzene in 250 ml of DMI was added to the flask over one hour. The resulting mixture was maintained at a temperature of from 145° to 150° C. for 5 hours, while distilling away the xylene. Then, the mixture was heated to a temperature of 170° to 180° C. and maintained at that temperature for 18 hours to accomplish the condensation.

Immediately after the completion of the reaction, the reaction mixture was distilled under a vacuum of 50 to 70 mmHg by an aspirator to recover 690 ml of DMI solvent. The residue was thrown into 1.5 l of water under vigorous stirring. A brown oil layer was separated as a lower layer. The brown oil comprised crude 1,3-bis(3-aminophenoxy)-5-chlorobenzene having a purity of 92.3% (determined by high-performance liquid chromatography). The two-layer mixture was left standing and decanted to obtain the brown oil. 520 g (2.5 mol) of a 6N aqueous solution of hydrochloric acid was added to the brown oil and the mixture was heated to form a solution. The solution was left standing and cooled at an ambient temperature to precipitate 1,3-bis(3-aminophenoxy)-5-chlorobenzene hydrochloride. The mixture was filtered. The resulting filter cake was washed with a 10% aqueous solution of sodium chloride and dried to obtain 174.4 g of 1,3-bis(3-aminophenoxy)-5-chlorobenzene hydrochloride (yield: 87.3%). This product was recrystallized from isopropanol containing 2% of water to obtain a pure white needle crystal. (m.p. 268°–272° C.)

Elemental analysis ($C_{18}H_{17}N_2O_2Cl_3$)

|  | C | H | N | Cl |
|---|---|---|---|---|
| calculated (%) | 54.09 | 4.29 | 7.01 | 26.61 |
| observed (%) | 53.92 | 4.34 | 7.0 | 26.59 |

Pure 1,3-bis(3-aminophenoxy)-5-chlorobenzene hydrochloride was dissolved in water and neutralized with a dilute aqueous solution of ammonia to liberate 1,3-bis(3-aminophenoxy)-5-chlorobenzene as a slightly brown oil.

The liberated 1,3-bis(3-aminophenoxy)-5-chlorobenzene was extracted with ether and dried in vacuo to obtain a slightly brown oil as a product. The oil was stored in a cold place to obtain a crystal (m.p. 72°–73° C.).

Elemental analysis ($C_{18}H_{15}N_2O_2Cl$)

|  | C | H | N | Cl |
|---|---|---|---|---|
| calculated (%) | 66.16 | 4.63 | 8.57 | 10.85 |
| observed (%) | 66.00 | 4.82 | 8.39 | 10.78 |

IR spectrum (KBr tablet) ($cm^{-1}$) 3460, 3390, 1630, 1605, 1585, 1500, 1445, 1320, 1290, 1185, 1165, 1015, 1000.

Mass spectrum (M/e) $M^+$ 326, 290, 217, 183

EXAMPLE 2

120 g (1.1 mol) of 3-aminophenol, 59.5 g (1.1 mol) of sodium methoxide and 500 ml of N-methylpyrrolidone were charged in the same apparatus as described in Example 1. The temperature of the content was raised under stirring while passing gaseous nitrogen through it. When the internal temperature reached 67° C., methanol began to be distilled away. The temperature was raised slowly while distilling away methanol. When the internal temperature reached 120° C., 91 g (0.5 mol) of 1,3,5-trichlorobenzene was added. The amount of methanol distilled away was 38 ml. The content was heated to 170° to 180° C. and maintained at that temperature for 15 hours to accomplish the condensation. Then the reaction mixture was treated according to the same procedure as described in Example 1 to obtain 170 g of 1,3-bis(3-aminophenoxy)-5-chlorobenzene hydrochloride (yield: 85%).

EXAMPLE 3

32.7 g (0.3 mol) of 3-aminophenol, 18.2 g (0.1 mol) of 1,3,5-trichlorobenzene, 28 g (0.2 mol) of anhydrous potassium carbonate and 150 ml of hexamethylphosphoric triamide were charged in a flask equipped with a stirrer. The mixture was maintained at 180° to 190° C. for 24 hours under stirring while passing gaseous nitrogen through it to accomplish the condensation. Then the reaction mixture was treated according to the same procedure as described in Example 1 to obtain 34.4 g of 1,3-bis(3-aminophenoxy)-5-chlorobenzene hydrochloride (yield: 85.8%).

EXAMPLE 4

12 g (0.11 mol) of 3-aminophenol, 4.6 g (0.11 mol) of granular potassium hydroxide of a purity of 96%, 10 ml of toluene and 50 ml of DMI were charged in the same apparatus as described in Example 1. The temperature of the content was raised under stirring while passing gaseous nitrogen through it, so that the toluene was refluxed to remove the water which generated in the reaction system by a water separator. 50 ml of DMI and 15.7 g (0.05 mol) of 1,3,5-tribromobenzene was added. The resulting mixture was maintained at 150° to 160° C. for 20 hours to accomplish the condensation, while distilling away the toluene contained in the system. Then the reaction mixture was treated according to the same procedure as described in Example 1 to obtain 16.8 g of 1,3-bis(3-aminophenoxy)-5-bromobenzene hydrochloride (yield: 75.7%).

This product was recrystallized from isopropanol containing 2% of water to obtain a slightly brown needle crystal as a pure product (m.p. 273°–277° C.).

Elemental analysis ($C_{18}H_{17}N_2O_2BrCl_2$)

|  | C | H | N | Br | Cl |
|---|---|---|---|---|---|
| calculated (%) | 48.67 | 3.86 | 6.31 | 17.99 | 15.97 |
| observed (%) | 48.57 | 3.92 | 6.21 | 17.73 | 15.9 |

The resulting pure 1,3-bis(3-aminophenoxy)-5-bromobenzene hydrochloride was dissolved in water and neutralized with a dilute aqueous solution of ammonia to liberate 1,3-bis(3-aminophenoxy)-5-bromobenzene. The liberated 1,3-bis(3-aminophenoxy)-5-bromobenzene was extracted with ether and dried in vacuo to obtain a slightly brown oil as a product. The oil was stored in a cold place to form a crystal (m.p. 68°–69° C.).

Elemental analysis ($C_{18}H_{15}N_2O_2Br$)

|  | C | H | N | Br |
|---|---|---|---|---|
| calculated (%) | 58.24 | 4.07 | 7.55 | 21.53 |
| observed (%) | 58.09 | 4.18 | 7.48 | 21.45 |

IR spectrum (KBr tablet) ($cm^{-1}$) 3460, 3340, 1625, 1605, 1585, 1500, 1460, 1320, 1290, 1185, 1165, 1015, 1000

Mass spectrum (M/e) M+ 370, 290, 154

EXAMPLE 5

12 g (0.11 mol) of 3-aminophenol, 7.2 g (0.11 mol) of granular potassium hydroxide having a purity of 86%, 11.3 g (0.05 mol) of 1-bromo-3,5-dichlorobenzene, 10 ml of benzene and 100 ml of N-methylpyrrolidone were charged in the same apparatus as described in Example 1. The temperature of the content was raised under stirring while passing gaseous nitrogen through it. The internal temperature was raised to 120° C., while azeotropically distilling away water along with the benzene. The content was maintained at that temperature for 5 hours. Then, the internal temperature was raised to 170° to 180° C. and the content was maintained at that temperature for 12 hours to accomplish the condensation.

The reaction mixture was treated according to the same procedure as described in Example 1 to obtain 16.3 g of 1,3-bis(3-aminophenoxy)-5-chlorobenzene hydrochloride (yield: 81.5%). This product was recrystallized from isopropanol containing 2% of water to obtain a while needle crystal (m.p. 267°–268° C.).

Elemental analysis ($C_{18}H_{17}N_2O_2Cl_3$)

|  | C | H | N | Cl |
|---|---|---|---|---|
| calculated (%) | 54.09 | 4.29 | 7.01 | 26.61 |
| observed (%) | 53.98 | 4.40 | 6.92 | 26.47 |

EXAMPLE 6

12 g (0.11 mol) of 3-aminophenol, 13.5 g (0.05 mol) of 1,3-dibromo-5-chlorobenzene, 10.4 g (0.075 mol) of potassium carbonate and 100 ml of dimethyl sulfoxide were charged in a flask equipped with a stirrer. The content was heated to a temperature of 150° to 170° C. and maintained at that temperature for 24 hours to accomplish the condensation.

The reaction mixture was treated according to the same procedure as described in Example 1 to obtain 13.6 g of 1,3-bis(3-aminophenoxy)-5-halogenobenzene hydrochloride.

This product was neutralized and then analyzed with a high-peformance liquid chromatography to reveal that the product comprised 1,3-bis(3-aminophenoxy)-5-chlorobenzene and 1,3-bis(3-aminophenoxy)-5-bromobenzene in a ratio of 93 to 7.

What is claimed is:

1. A process for the preparation of 1,3-bis(3-aminiophenoxy)-5-halogenobenzene represented by the general formula (I):

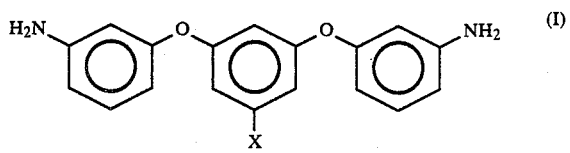

wherein X is a chlorine or bromine atom, which comprises reacting 1,3,5-trihalogenobenzene represented by the general formula (II):

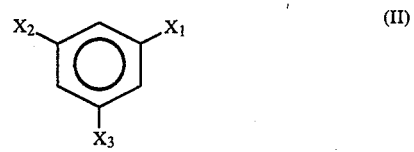

wherein $X_1$, $X_2$ and $X_3$ are each a chlorine or bromine atom, with 3-aminophenol in the presence of a dehydrohalogenating agent in an aprotic polar solvent and in the absence of an Ullmann reaction accelerator.

2. A process of claim 1 wherein the dehydrohalogenating agent is a hydroxide, carbonate, bicarbonate or alkoxide of an alkali metal.

3. A process of claim 1 wherein the reaction temperature is from 120° to 240° C.

4. The process of claim 1, including the step of:
   (a) selecting said solvent from the group consisting of N-methyl formamide, N,N-dimethyl formamide, N,N-dimethyl acetamide, dimethyl sulfone, sulfolane, dimethyl sulfoxide, N-methylpyrrolidone, 1,3-dimethyl-2-imidazolidinone and hexamethyl phosphoric triamide.

5. The process of claim 1, including the step of:
   (a) selecting the dehydrohalogening agent from the group consisting of potassium hydroxide, sodium hydroxide, lithium hydroxide, potassium carbonate, sodium carbonate, lithium carbonate, potassium bicarbonate, sodium bicarbonate, potassium ethoxide, potassium isopropoxide, sodium methoxide, sodium ethoxide, lithium ethoxide and mixtures thereof.

6. The process of claim 1, including the step of:
   (a) providing 3-aminophenol in an amount of from about 2 to about 5 times the amount of 1,3,5-trihalogenobenzene.

7. The process of claim 6, including the step of:
   (a) providing 3-aminophenol in an amount of from about 2.1 to about 3.0 times the amount of 1,3,5-trihalogenobenzene.

8. The process of claim 1, including the step of:
(a) providing the dehydrohalogenating agent in an amount of from about 1 to about 1.5 times the amount of 3-aminophenol.

9. The process of claim 1, including the step of:
(a) removing water generated by the reactants.

10. The process of claim 9, including the step of:
(a) removing water generated by the reactants through azeotropic distillation.

11. The method of preparing 1,3-bis(3-aminophenoxy)-5-halogenobenzenes, comprising the steps of:
(a) reacting 1,3,5-trihalogenobenzene selected from the group consisting of 1,3,5-trichlorobenzene, 1,3,5-tribromobenzene, 1-bromo-3,5-dichlorobenzene and 1,3-dibromo-5-chlorobenzene with 3-aminophenol in the presence of a dehydrohalogenating agent selected from the group consisting of potassium hydroxide, potassium carbonate and sodium methoxide in an aprotic polar solvent selected from the group consisting of dimethyl sulfoxide, N-methyl pyrrolidone, 1,3-dimethyl-2-imidazolidinone and hexamethyl phosphoric triamide and in the absence of an Ullman reaction accelerator.

12. The process of claim 11, including the step of:
(a) maintaining the reactants at a temperature of from about 140° C. to about 220° C.;
(b) providing 3-aminophenol in an amount of from about 2 to about 5 times the amount of 1,3,5-trihalogenobenzene; and,
(c) providing the dehydrohalogenating agent in an amount of from about 1 to about 1.5 times the amount of 3-aminophenol.

13. The process of preparing 1,3-bis(3-aminophenoxy)-5-halogenobenzene, comprising the steps of:
(a) charging 3-aminophenol, a dehydrohalogenating agent and an aprotic solvent into a reaction vessel and therein converting the 3-aminophenol into its alkali metal salt; and,
(b) adding 1,3,5-trihalogenobenzene into the vessel so that the 1,3,5-trihalogenobenzene is condensed in the absence of an Ullman accelerator.

14. The process of claim 13, including the step of:
(a) removing water generated by the reactants from the reaction vessel.

15. The process of preparing 1,3-bis(3-aminophenoxy)-5-halogenobenzene, comprising the steps of:
(a) charging 3-aminophenol, a dehydrohalogenating agent, an aprotic solvent and 1,3,5-trihalogenobenzene into a reaction vessel;
(b) heating the reactants to a temperature of from about 140° C. to about 220° C. and thereby condensing the 1,3,5-trihalogenobenzene in the absence of an Ullman accelerator; and,
(c) removing water generated by the reactants from the charging vessel.

16. The process of claim 15, including the steps of:
(a) providing 3-aminophenol in an amount of from about 2 to about 5 times the amount of 1,3,5-trihalogenobenzene; and,
(b) providing the dehydrohalogenating agent in an amount of from about 1 to about 1.5 times the amount of 3-aminophenol.

* * * * *